United States Patent [19]
Pyke et al.

[11] Patent Number: 4,761,639
[45] Date of Patent: Aug. 2, 1988

[54] LIGHTWEIGHT, COMPACT DETECTOR OF SUDDEN CHANGES IN CONCENTRATION OF A GAS

[75] Inventors: Stephen C. Pyke, Willowick; Donald L. Boos, Garfield Heights; Michael T. McMahon, Sebring, all of Ohio

[73] Assignee: The Standard Oil Company, Cleveland, Ohio

[21] Appl. No.: 916,668

[22] Filed: Oct. 8, 1986

Related U.S. Application Data

[63] Continuation-in-part of Ser. No. 811,548, Dec. 20, 1985, abandoned.

[51] Int. Cl.$^4$ .............................................. G08B 17/10
[52] U.S. Cl. ..................................... 340/634; 340/661; 73/23
[58] Field of Search ............... 340/632, 633, 634, 661, 340/629; 73/23, 19; 338/34

[56] References Cited

U.S. PATENT DOCUMENTS

| | | | |
|---|---|---|---|
| 3,611,335 | 10/1971 | Ogden et al. ...................... | 340/629 |
| 3,831,432 | 8/1974 | Cox .................................... | 73/23 |
| 3,901,067 | 8/1975 | Boardman, Jr. et al. ............ | 73/23 |
| 4,039,852 | 8/1987 | Miyamoto ........................... | 340/633 |
| 4,058,368 | 11/1977 | Svensson et al. .................. | 73/23 |
| 4,198,851 | 7/1980 | Janata ................................ | 73/23 |
| 4,205,307 | 5/1980 | Liermann ........................... | 340/644 X |

Primary Examiner—Joseph A. Orsino
Assistant Examiner—Jeffery A. Hofsass
Attorney, Agent, or Firm—Jeffrey A. Wyand; Joseph G. Curatolo; Larry W. Evans

[57] ABSTRACT

Lightweight, compact apparatus for detecting sudden changes in the concentration of at least one selected gas provides a warning when said gas concentration increases suddenly. In one embodiment, a chemically sensitive field effect transistor provides a sensing signal two amplifiers having different overall gains and widely different time constants. Detection of sudden gas concentration changes causes the relative magnitudes of the amplifier output signals to be inverted triggering a warning. The apparatus may occupy less than 1.25 cubic inches and weigh less than 4 ounces so that it may be worn by an individual throughout his work place.

16 Claims, 2 Drawing Sheets

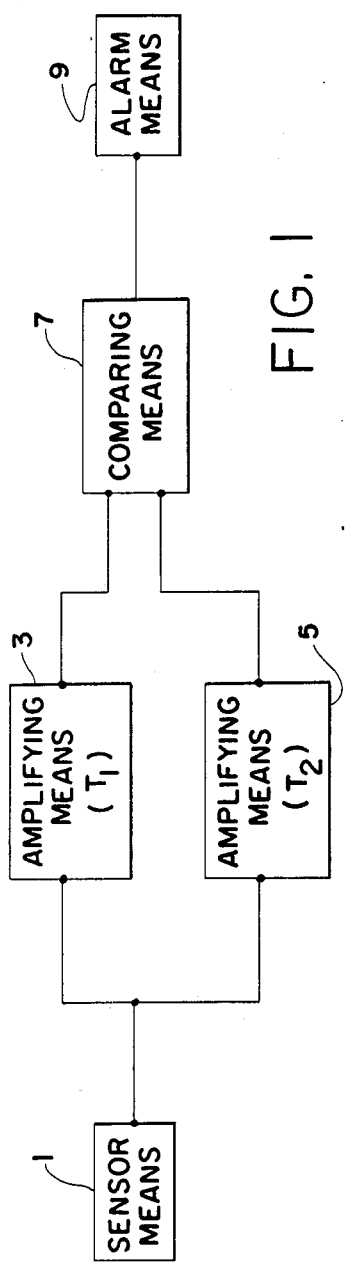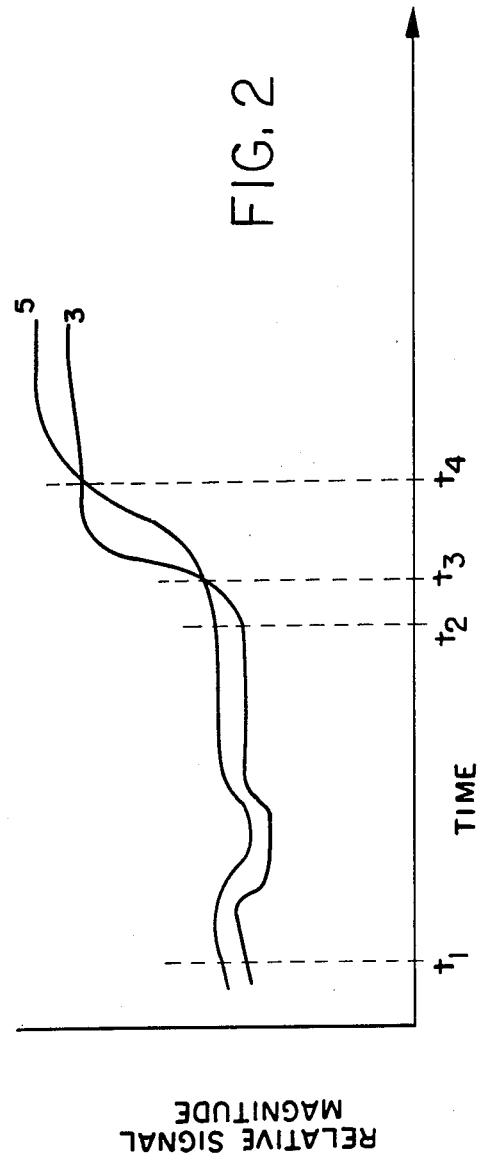

$T_2 \ll T_1$ ered in this application by reference. The power con-
LIGHTWEIGHT, COMPACT DETECTOR OF SUDDEN CHANGES IN CONCENTRATION OF A GAS This application is a continuation-in-part of U.S. patent application Ser. No. 811,548, filed Dec. 20, 1985, now abandoned.

BACKGROUND

Gas monitors and gas detection devices are well-known as analytical tools and for detecting the presence of a particular gas in the workplace. The known devices operate on various principles employing optical, chemical, chromatographic, electrochemical, and catalytic techniques to detect specific gases. Optical devices detect infrared absorption spectra, are expensive and not portable. They are not capable of continuous monitoring. Chemical reaction devices, such as calorimetric systems and gas chromatography analyzers are also expensive, bulky and cannot continuously monitor the environment. Electrochemical real time gas detection usually occurs in a cell containing gas dissolved in an electrolyte. This method of detection is not highly selective, the electrolyte is susceptible to freezing and the process consumes relatively large amounts of power. Catalytic sensors generally rely on a thermal sensor that measures the temperature change of a catalytic material or a semiconductor catalytic sensor. Semiconductor sensors used in such detectors include zirconium oxide, titanium oxide, indium oxide, tin oxide, tungsten oxide, platinum and palladium doped metal oxides, and mixtures of them. Impedance changes in the oxide indicate the occurrence of a catalytic reaction.

All of the cited gas detectors are large and/or consume relatively large amounts of electrical power. As a result, these detectors, if portable at all, require rather large and heavy batteries as portable power supplies. Therefore, these gas detectors are not conveniently used by personnel in the way film badges and other dosimeters are. In fact, the smallest portable gas detector presently available is about the size of a package of cigarettes and weighs about one half pound (225 gms.) It is highly desirable to make a smaller and lighter weight gas selective detector that may be continuously and conveniently worn by an individual.

Silicon field effect transistors having sensitivities to particular gases have been reported by Lundstrom et al. in Applied Physics Letters, Vol. 26, No. 2, Jan. 15, 1975. More recently, suspended gate chemically sensitive field effect transistors have been disclosed in U.S. Pat. Nos. 4,411,741 and 4,514,263 to Janata and 4,456,522 and 4,486,292 to Blackburn. Those patents are incorporated in this application by reference. The power consumption of these so-called CHEMFETS is very small so that a lightweight battery can power a CHEMFET for a long time.

SUMMARY OF THE INVENTION

With the advent of the CHEMFET, specific gas detectors of a size and weight that can be conveniently and continuously worn by an individual are feasible. The invention provides such a detector that may occupy no more than 1.25 cubic inches (20 cubic centimeters) and weigh no more than 4 ounces (125 grams) The novel detector warns its wearer of detected sudden, relative increases in the concentration of a selected gas so that he can leave an area of danger. Such warnings supplement the functions of stationary monitors that can measure the absolute quantity of gas in a fixed location and warn of slowly or rapidly rising concentrations of dangerous gases in that location. The novel detector provides protection to a mobile worker as he moves throughout his workplace during his working day within and beyond the range of stationary gas monitors. The detector may include a single sensor for a toxic, combustible or otherwise potentially hazardous gas or an array of detectors for sensing a number of potentially hazardous gases.

BRIEF DESCRIPTION OF THE DRAWINGS

FIG. 1 is a block diagram of an embodiment of the invention.

FIG. 2 is a graph of the response over time of an embodiment of tne invention.

DETAILED DESCRIPTION OF PREFERRED EMBODIMENTS

Figure 3:
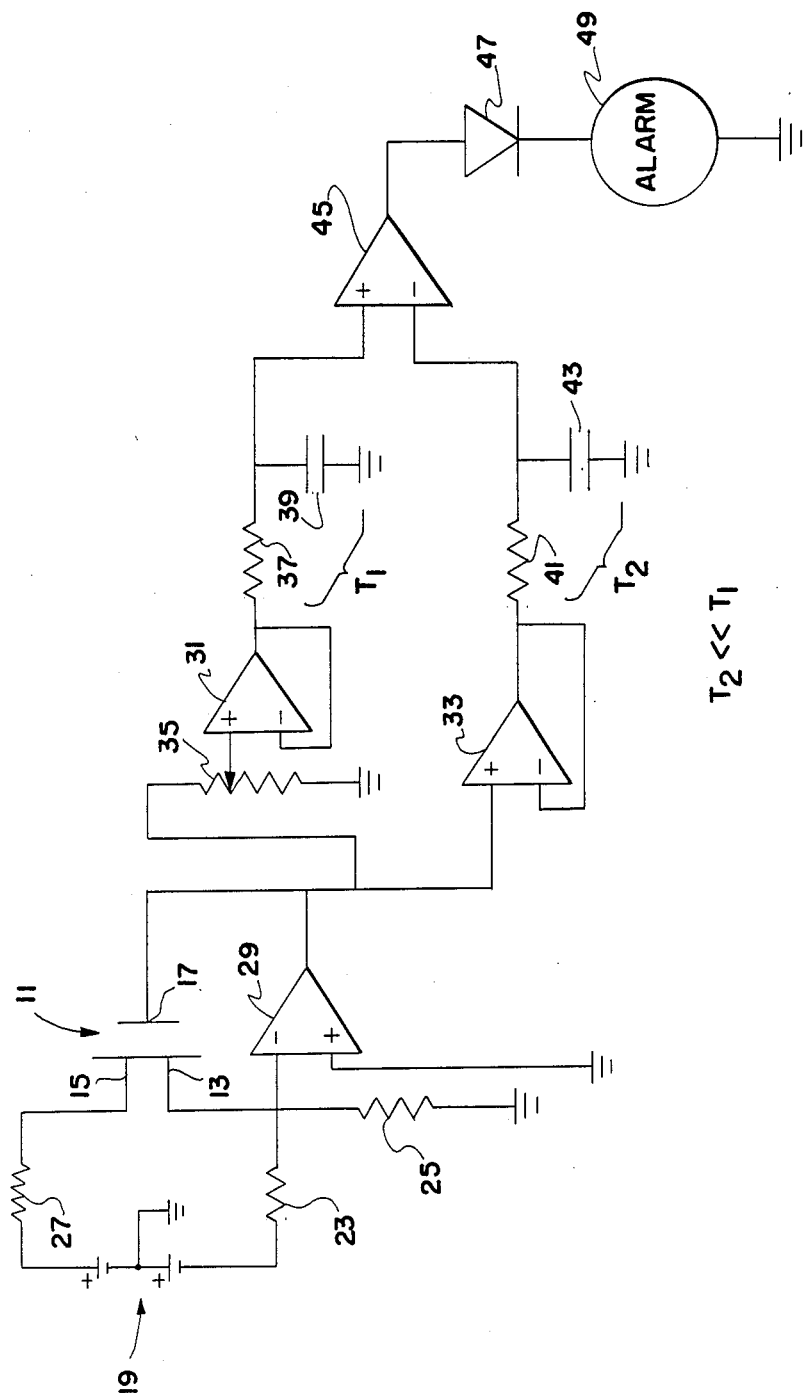
FIG. 3 is a schematic circuit diagram of an embodiment of the invention.

FIG. 1 is a block diagram of an embodiment of the invention to illustrate its functioning. Block 1 represents a sensor that responds to the detection of a particular gas by producing a change in an electrical sensing signal. That sensing signal is supplied directly to an amplifying means 3 and to an amplifying means 5 that has higher overall gain than means 3. Amplifying means 3 and 5 have different time constants, $T_1$ and $T_2$, respectively, that control the rates at which their output signals can change over time in response to changes in their input signals. $T_1$ is much smaller than $T_2$, preferably smaller by a factor of 100 or more. The output signals from amplifying means 3 and 5 are applied, respectively, to different input terminals of a comparing means 7. The output signal generated by comparing means 7 has one polarity, i.e. positive or negative, when a particular one of the two input signals is larger in magnitude than the other, and the opposite polarity when the relative magnitudes of the input signals are inverted.

In a steady state or quasi-steady state situation, e.g. from time $t_1$ to time $t_2$ in FIG. 2, there is an approximately constant difference between the magnitudes of the input signals applied to comparing means 7 with the result that the output signal of comparing means 7 has a fixed polarity. When the amplitude of the sensing signal changes in response to detection of gas, the output signals of amplifying means 3 and 5 change, with the output signal from means 5 changing more slowly than that from means 3. In the presence of a large, sudden change in the sensing signal, e.g. at time $t_3$, the relative magnitudes of the output signals from amplifying means 3 and 5 supplied to comparing means 7 reverses, so that the polarity of its output signal changes. Eventually, at time $t_4$, the magnitude of the output signal from amplifying means 5 catches up to and overtakes the magnitude of the output signal from means 3, restoring the original polarity of the output signal from comparing means 7. That is, after the inversion of the relative magnitudes of the output signals from amplifying means 3 and 5, the relative magnitudes are reversed to their initial relationship. In the period from time $t_3$ to time $t_4$, an alarm means 9 responsive to one polarity of the signal received from comparing means 7, produces a warning.

A further, more specific embodiment of the invention is shown in FIG. 3. The embodiment of FIG. 3, like that of FIG. 1, produces a warning upon detection of a sudden change in the concentration of the gas being monitored. The embodiment of FIG. 3 includes a simple semiconductor sensor 11 that is sensitive to one gas. From the description that follows, one of skill in the art will be able to construct a detector incorporating an array of such sensors, each sensor being sensitive to a different gas. Such detectors might be no more than multiple embodiments of the detector circuitry of FIG. 3, perhaps with a single alarm, or one signal processing circuit with multiple sensors connected to it through a multiplexer. The description that follows, however, makes reference to a detector including a single sensor that is sensitive to one gas, without limiting the scope of the invention.

Sensor 11 is preferably a field effect transistor, for example, one of the types described in the patents cited above. The gate electrode of such a device reacts to the presence of a selected gas producing an electrical response that can be detected and processed in electronic circuitry. For example, a noble metal gas like palladium or platinum responds to the presence of hydrogen. Similarly, it is known that gold is sensitive to hydrogen sulfide, and that nickel and zirconium are sensitive to carbon monoxide. CHEMFETS sensitive to hydrogen, hydrogen sulfide, methane, carbon monoxide, oxygen, alcohols, water vapor, various low molecular weight hydrocarbons and other gaseous compounds can be manufactured for use in the novel apparatus.

In FIG. 3, chemically sensitive field effect transistor 11 includes a source electrode 13, a drain electrode 15 and a gate electrode 17. Source 13 and drain 15 are connected to a power supply 19 that has a center ground 21. Power supply 19 can supply plus and minus voltages, for example, plus and minus 9 volts. Source 13 may be maintained at a negative bias, for example $-3$ volts, by connection to the negative terminal of power supply 19 through a resistor 23. If regulation of the source bias voltage is desired, a resistor 25 may be connected between source 13 and ground. If careful regulation of the source bias is important, resistor 25 can be replaced by a zener diode reversed biased in the conventional manner. Drain 15 is given a positive bias, for example 6 volts, by connection to the positive terminal of power supply 19 through a resistor 27. If close regulation of this bias voltage is desired, a zener diode can be added and connected from drain 15 to ground.

Source 13 is connected to the negative sense input terminal of an operational amplifier 29 which has its positive sense input terminal grounded. Gate electrode 17 is connected to the output terminal of operational amplifier 29. When the selected gas to which sensor 1 responds enters the gate region, the electric field beneath the gate is modified. Generally, gate 17 becomes more positive and, in any event, the current flowing between the source and drain is changed. Operational amplifier 29 acts as a constant current source and responds to a changed source-drain current, indicated by a change in voltage drop across resistor 25, by changing the voltage on gate 17 to restore the current to its original value. That is, the sensing signal at the output of amplifier 29 changes the gate voltage. The rate of that response can be adjusted by connecting a capacitor (not shown) between the output terminal and negative sense input terminal of operational amplifier 29, but the integration step provided by that capacitor is not essential.

The sensing signal from amplifier 29 is applied to the positive sense input terminals of two operational amplifiers 31 and 33. Amplifiers 31 and 33 may be a matched pair of amplifiers whose overall gains are made unequal or may be amplifiers whose gains are inherently unequal. In the former situation, shown in FIG. 3, the sensing signal reaches amplifier 31 through a resistive, variable voltage divider 35 having one end grounded and its variable terminal connected to the positive sense input terminal of amplifier 31. That is, a less than unity fraction of the sensing signal is applied to amplifier 31 while the unreduced sensing signal is applied to amplifier 33, giving the amplifiers different overall gains with respect to the sensing signal. The output terminals of amplifiers 31 and 33 are directly connected to their respective negative sense input terminals so that the amplifiers function as unity gain impedance transformers. In the circuitry shown, the magnitude of the output signal at amplifier 31 is smaller than the magnitude of the output signal of amplifier 33 by an amount determined by the setting of voltage divider 35.

The output terminals of amplifiers 31 and 33 are each connected to separate impedance networks. The embodiment of FIG. 3 shows an RC impedance network with a resistor 37 connected to the output terminal of amplifier 31. A capacitor 39 is connected from resistor 37 opposite amplifier 31 to ground. Likewise, a similar RC network consisting of a resistor 41 and capacitor 43 is connected to the output of amplifier 33, with one terminal of capacitor 43 grounded. The time constants of each RC network shown is the product of its capacitance and resistance. The time constants of each networks are chosen to be different by a factor of at least 100, and preferably by a factor of 1000 or more. Exemplary values of resistors 37 and 41 are 500K ohms, while capacitors 39 and 43 may be 2 microfarads and 0.02 microfarads, respectively. Because of the time constant differences, when a transient signal is applied to the inputs of amplifiers 31 and 33, the resulting transient signals at the outputs of the two networks will change at different rates.

In the steady state and quasi-steady state, the magnitude of the signal at capacitor 39 will be smaller than the magnitude of the signal at capacitor 43. However, if the time constant of network 41, 43 is much larger than that of network 37, 39, the magnitude of the signal at capacitor 39 can temporarily exceed the magnitude of the signal at capacitor 43 when responding to a transient signal having a sufficiently large and rapid change of magnitude. This effect results from the slower response time of the longer time constant network. That is, in responding to a transient signal, the relative magnitudes of the output signals may become inverted, before being reversed to restore their initial relationship.

It is noted that for the invention to be operable, a particular embodiment must be designed so that the reversal in relative magnitudes just described can occur. That is, the shorter time constant network must be put in the appropriate amplifying channel taking into account the relative overall gain of each of the channels, the initial sense of the two channel output signals and the direction and amount of change of the channel output signal magnitudes upon detection of sudden changes in gas concentration.

The processed signals are applied to a differential amplifier 45. In the embodiment of FIG. 1, the signal from capacitor 39 is connected to the positive sense input terminal of amplifier 45 and the signal from capacitor 43 is applied to the negative sense input terminal of amplifier 45. Amplifier 45 produces an output signal that has a polarity, i.e. positive or negative magnitude, that indicates which of the two input signals is larger. For example, the output signal from amplifier 45 may be negative when the signal from capacitor 43 is larger in magnitude than the signal from capacitor 39 and vice versa. Thus, when the relative magnitudes of these signals are inverted, the polarity of the output signal from amplifier 45 is inverted.

The output terminal of amplifier 45 is connected to a terminal of a switch, shown as a diode 47. In the embodiment illustrated, the output terminal of amplifier 45 is connected to the anode of diode 47. Thus when the output signal from amplifier 45 is negative, the normal steady state situation for the embodiment illustrated, diode 47 is open. But when the relative magnitudes of the input signals to amplifier 45 are inverted, the polarity of the output signal, then the alarm signal, of amplifier 45 is inverted, causing diode 47 to conduct, i.e. closing the switch.

Switch 47 is connected to an alarm 49 that responds to an alarm signal by producing a visual and/or audible warning. An audible warning might be produced by an piezoelectric transducer. A visual alarm might be produced by a light emitting diode. Switch 47 cancels the warning when the initial magnitude relationship of the capacitor output signals is restored, i.e. when the alarm signal ceases. The connection through switch 47 is necessary if alarm 49 is activated by the presence of any input signal. If alarm 49 responds to only one polarity of input signal, switch 47 may be unnecessary. Likewise, switch 47 could be normally closed, as by reversing its polarity, and open upon generation of an alarm signal if alarm 49 is triggered by the absence of a signal. In any event, when an alarm switch is present, it is actuated only while an alarm signal is being generated.

From this description, it can be understood that the novel detector only responds to detected sudden increases in gas concentration. Relatively slowly occurring increases or decreases in gas concentration merely result in gradual changes in the magnitudes of the compared output signals. These gradual changes do not produce an inversion of the magnitudes of those signals and therefore do not produce a warning. Likewise, the alarm shown in FIG. 3 is turned off once the steady state or quasi-steady state condition is restored. Therefore, the novel detector supplements other monitors that track absolute concentrations of hazardous gases and is ideal for warning a mobile employee upon his entering into a hazardous area. Alarm 49 is likely to be the largest power consumer in the detector. In the embodiment shown, the alarm is automatically cancelled so that excessive power consumption is avoided. The sensitivity of the detector and duration of the alarm is determined, in part, by the selection of the time constants of the impedance networks and by the relative gains of the amplifying means, e.g. by the setting of voltage divider 35. Therefore, these characteristics can be adjusted both in the circuit design stage and during use in the field to produce a desired sensitivity.

Embodiments of the detector can be made in very small sizes and weights with discrete and hybrid element circuits. Power consumption is minimal if MOS components are used. All the operational amplifiers needed can be purchased in a single small, lightweight package, e.g. the LM124. This sort of package provides relative immunity against sensitivity changes with changes in temperature, and other ambient conditions. A hybrid circuit embodiment can be made that occupies no more than 1.25 cubic inches (20 cubic centimeters) and weighs less than 4 ounces (125 grams). Most of that size and weight is attributable to the battery power supply. By using custom made integrated circuits, the detector can be further reduced in size and weight to that of the now-common electronic wristwatch, e.g. no more than 0.375 cubic inches (6 cubic centimeters) in volume and 2 ounces (60 grams) in weight. Weights as little as 1 ounce (28 grams) are easily achievable. The reductions in size and weight provided by the invention represents a breakthrough that is vital to personal use of a gas detector.

The invention has been described with respect to certain preferred embodiments. Various additions and modifications within the spirit of the invention will occur to those of skill in the art. Accordingly, the scope of the invention is limited solely by the following claims.

We claim:

1. Apparatus for signalling a sudden increase in the concentration of a selected gas comprising:
   sensor means for producing a change in an electrical sensing signal in response to the detection of a change in the concentration of a selected gas;
   first and second amplifying means of unequal overall gain, each amplifying means receiving said sensing signal and having substantially different time constants, for generating first and second output signals, respectively, in response to said sensing signal;
   means for comparing the magnitude of said first output signal to the magnitude of said second output signal and for generating an alarm signal when the relative magnitudes of said first and second output signals are inverted; and
   means receiving said alarm signal for producing a warning in response to the generation of an alarm signal.

2. The apparatus of claim 1 wherein said sensor means comprises a field effect transistor having source, drain and gate electrodes that is electrically responsive to said selected gas.

3. The apparatus of claim 2 including a constant current source for establishing a constant current flow between said source and drain electrodes.

4. The apparatus of claim 2 including means for detecting changes in the current flowing between said source and drain electrodes to generate said sensing signal.

5. The apparatus of claim 4 wherein said means for detecting changes comprises a resistor connected in series with one of said source and drain electrodes.

6. The apparatus of claim 1 including dividing means for connecting a reduced portion of said sensing signal to one of said first and second amplifying means for effectively reducing the overall gain of said one of said first and second amplifying means.

7. The apparatus of claim 1 wherein the time constant of one of said first and second amplifying means is at least 100 times larger than the time constant of the other of said first and second amplifying means.

8. The apparatus of claim 1 wherein said means for comparing and for generating includes means receiving both of said first and second output signals for generating at an output terminal a polarity signal having a polarity indicative of the relative magnitudes of said first and second output signals, one of said polarities being said alarm signal.

9. The apparatus of claim 1 wherein said means for producing a warning includes means for cancelling said warning when the relative magnitudes of said first and second output signals is reversed after being inverted.

10. The apparatus of claim 9 wherein said means for comparing and for generating includes means receiving both of said first and second output signals for generating at an output terminal a polarity signal having a polarity indicative of the relative magnitudes of said first and second output signals, one of said polarities being said alarm signal.

11. The apparatus of claim 10 wherein said means for producing a warning includes an alarm and said means for cancelling includes a switch connected between said output terminal and said alarm, said switch being activated while said alarm signal is generated.

12. The apparatus of claim 1 wherein said means for producing a warning includes an alarm producing an audible warning.

13. The apparatus of claim 1 wherein said means for producing a warning includes an alarm producing a visual warning.

14. A portable electrical apparatus for signalling a sudden increase in the concentration of a selected gas comprising:
- a chemically sensitive field effect transistor for producing a change in an electrical sensing signal in response to the detection of a change in the concentration of a selected gas;
- first and second amplifiers having unequal overall gains ans substantially different time constants, each amplifier receiving said sensing signal, for generating first and second output signals, respectively, in response to said sensing signal;
- means for comparing the magnitude of said first output signal to the magnitude of said second output signal and for generating an alarm signal when the relative magnitudes of said first and second output signals are inverted;
- an alarm receiving said alarm signal for producing a warning in response to the generation of an alarm signal; and
- a battery for supplying electrical power to said apparatus.

15. The apparatus of claim 14 wherein said apparatus occupies a volume of no more than 1.25 cubic inches.

16. The apparatus of claim 14 wherein said apparatus weighs no more that 4 ounces.

* * * * *